US005151271A

United States Patent [19]

Otsuka et al.

[11] Patent Number: 5,151,271

[45] Date of Patent: Sep. 29, 1992

[54] PRESSURE-SENSITIVELY ADHERING COMPOSITE MEDICINAL PREPARATION

[75] Inventors: Saburo Otsuka; Yuusuke Ito; Toshiyuki Yoshikawa; Shoichi Tokuda, all of Ibaraki, Japan

[73] Assignee: Nitti Electric Industrial Co., Ltd., Osaka, Japan

[21] Appl. No.: 426,526

[22] Filed: Oct. 24, 1989

Related U.S. Application Data

[60] Division of Ser. No. 224,214, Jul. 25, 1988, abandoned, which is a continuation of Ser. No. 406,726, Aug. 9, 1982, abandoned.

[30] Foreign Application Priority Data

Aug. 27, 1981 [JP] Japan ............ 56-134888
Aug. 27, 1981 [JP] Japan ............ 56-134889

[51] Int. Cl.[5] ............ A61F 13/00
[52] U.S. Cl. ............ 424/443; 424/448
[58] Field of Search ............ 604/896, 897, 892, 890; 428/343, 355; 424/16, 19-22, 28

[56] References Cited

U.S. PATENT DOCUMENTS

| | | | |
|---|---|---|---|
| 3,122,475 | 2/1964 | Schaeppi | 424/21 |
| 3,699,963 | 10/1972 | Zaffaroni | 604/897 |
| 3,742,951 | 7/1973 | Zaffaroni | 604/897 |
| 3,797,494 | 3/1974 | Zaffaroni | 604/897 |
| 4,031,894 | 6/1977 | Urquhart et al. | 604/897 |
| 4,286,592 | 9/1981 | Chandrasekaran | 604/897 |
| 4,340,043 | 7/1982 | Seymour | 128/132 |
| 4,420,470 | 12/1983 | Otsuka et al. | 424/28 |
| 4,460,369 | 7/1984 | Seymour | 604/897 |
| 4,483,846 | 11/1984 | Koide | 604/897 |

FOREIGN PATENT DOCUMENTS

| | | |
|---|---|---|
| 0013606 | 7/1980 | European Pat. Off. . |
| 0020777 | 1/1981 | European Pat. Off. . |
| 0040861 | 12/1981 | European Pat. Off. . |
| 0040862 | 12/1981 | European Pat. Off. . |
| 1228030 | 11/1966 | Fed. Rep. of Germany . |
| 2953327 | 11/1980 | Fed. Rep. of Germany . |
| 3111550 | 5/1982 | Fed. Rep. of Germany . |
| 3208853 | 9/1982 | Fed. Rep. of Germany . |
| 2824288 | 6/1987 | Fed. Rep. of Germany . |
| 1108837 | 4/1968 | United Kingdom . |
| 2021950 | 12/1979 | United Kingdom . |
| 1577259 | 10/1980 | United Kingdom . |
| 2073588 | 10/1981 | United Kingdom . |
| 2086224 | 5/1982 | United Kingdom . |
| 2087234 | 5/1982 | United Kingdom . |
| 2095108 | 9/1982 | United Kingdom . |
| 2093694 | 9/1986 | United Kingdom . |

OTHER PUBLICATIONS

Deanin; "Polymer Stu., Prop. & App."; Cahners Books; Boston; 1972 p. 154.

*Primary Examiner*—Thurman K. Page
*Assistant Examiner*—Leon R. Horne
*Attorney, Agent, or Firm*—Wenderoth, Lind & Ponack

[57] ABSTRACT

A pressure-sensitively adhering multilayer medicinal preparation comprises a pressure-sensitively adhering macromolecular substance layer and a polymer layer adjacent thereto and the drug and adjuvant incorporated in said preparation each can migrate from the layer of its original incorporation into the other, said adjuvant being capable of increasing absorption of the drug. In such preparation, the drug amount per unit volume can be increased.

11 Claims, No Drawings

PRESSURE-SENSITIVELY ADHERING COMPOSITE MEDICINAL PREPARATION

This application is a division of now abandoned application Ser. No. 224,214, filed Jul. 25, 1988, which application is, in turn, a continuation of now abandoned application Ser. No. 406,726, filed Aug. 9, 1982.

BACKGROUND OF THE INVENTION

1. Field of the Invention

This invention relates to a novel pressure-sensitively adhering medicinal preparation. More particularly, it relates to a pressure-sensitively adhering multilayer medicinal preparation capable of increasing drug supply to the skin per unit area and producing more efficient percutaneous drug absorption.

DESCRIPTION OF PRIOR ART

Various pressure-sensitively adhering composite medicinal preparations for percutaneous absorption of drugs have so far been proposed. They comprise a drug-containing macromolecular substance layer having pressure-sensitive adhesiveness at ordinary temperatures and a supporting member therefor.

Recent attempts to ensure the pharmacological actions of a drug or to increase the drug amount which can be incorporated per unit area comprise incorporating the drug into such pressure-sensitively adhering macromolecular substance to an extent of supersaturation. However, such excessive drug incorporation presents a problem that the drug crystallizes out on the macromolecular substance layer surface, whereby the pressure-sensitive adhesiveness is markedly decreased.

Further attempts to increase the drug amount per unit area consist of increasing the thickness of the macromolecular substance layer while reducing the level of drug incorporation to a level not to exceed the solubility limit. However, there remain problems. For instance, sufficient drug effect cannot be expected because of insufficient drug amount per unit area, or increased adhesiveness to the skin would result in pain at the time of peeling off, or the macromolecular substance often oozes out of the supporting member.

SUMMARY OF THE INVENTION

An object of the invention is to provide a novel composite preparation in which drug crystallization in the macromolecular substance layer can be prevented and with which an increased per-unit-area amount of drug can be supplied to the skin as a result of incorporation thereinto of an adjuvant capable of increasing percutaneous drug absorption without increasing the macromolecular substance layer thickness or without necessity of an increased drug concentration.

Another object of the invention is to provide a novel composite preparation in which improved percutaneous absorption, diffusion and solubility of drug are attained as a result of incorporation of an increased per-unit-volume amount of adjuvant capable of increasing percutaneous drug absorption and in which crystallization of said adjuvant can be prevented.

A third object of the invention is to provide a composite preparation in which the rate of drug activity expression, duration of effectiveness and other factors can be controlled in a relatively arbitrary manner.

Other objects of the invention will become clear from the description and examples which follow.

DETAILED DESCRIPTION OF INVENTION

The above objects can be achieved, in accordance with the invention, by a composite preparation characterized in that it comprises at least two layers, namely a layer of a macro-molecular substance having pressure-sensitive adhesiveness at ordinary temperatures and a polymer layer adjacent to said macromolecular substance layer, that at least one of the macro-molecular substance layer and polymer layer at least contains a percutaneously absorbable drug and the other at least contains an adjuvant capable of increasing percutaneous drug absorption, and that the drug and adjuvant respectively can migrate into the adjacent macromolecular substance layer and polymer layer.

In the practice of the invention, the polymer layer is only required to be adequately compatible with the drug and adjuvant, allow diffusion and migration of the drug and adjuvant in contact therewith and be in the form of film or sheet. No other particular requirements are essential for said layer. Preferably, however, said layer is a film (preferably having a thickness of about 10–1,000 microns) of a polymer or copolymer having a glass transition point (Tg) of not lower than −50° C., preferably −45° C. to +75° C., practically −40° C. to +45° C., or a polymer mixture containing at least 10 weight percent of such polymer or copolymer. Examples of said polymer or copolymer are polyvinyl acetate, copolymers of vinyl acetate and a monomer copolymerizable therewith and alkoxy (meth)acrylate-containing polymers. The monomer copolymerizable with vinyl acetate includes ethylene, acrylic acid esters and methacrylic acid esters. The alkoxy (meth)acrylate has the following formula

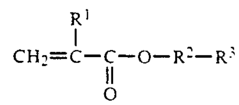

$$CH_2{=}C(R^1){-}C({=}O){-}O{-}R^2{-}R^3$$

wherein $R^1$ is a hydrogen atom or a methyl group, $R^2$ is an alkylene group containing 2–18 carbon atoms or a group of the formula: $(O-CH_2-CH_2)_n$ wherein n is 1 to 30 and $R^3$ is an alkoxy group containing 1–4 carbon atoms.

To said polymer, there may be added a natural rubber, a synthetic rubber such as silicone rubber, polyisobutylene rubber, chloroprene rubber or styrene-isoprene-styrene block copolymer rubber, or a synthetic resin such as a polyacrylic, polyurethane or polyolefin resin. The level of addition of such natural and/or synthetic rubber and/or synthetic resin should not exceed 90 weight percent. The resulting polymer mixture should preferably have a Tg of not lower than −50° C.

When the Tg is not lower than −50° C., the polymer allows an increased degree of diffusion therein of the drug and adjuvant, hence an increased extent of migration of the drug and adjuvant, but is not deteriorated in physical strength by the incorporation of adjuvant, drug and so on; the polymer is excellent in flexibility and scarcely irritates the skin and therefore is preferred.

The above polymer layer is preferably supported, on one side thereof, by a film or sheet substantially impermeable to the drug and adjuvant, whereby a self-supporting property is given to the composite preparation. Said film or sheet is made of polyacrylate, polyethylene, ethylene-vinyl acetate copolymer saponification product, polypropylene, polyvinylidene chloride, polyester, polyamide, cellophane or metal foil, for instance.

The macromolecular substance is required among others, to have pressure-sensitive adhesiveness at ordinary temperatures, to secure adhesion of the preparation to the skin for a required period of time, to be adequately compatible with the drug and adjuvant, to allow diffusion and migration of the drug and adjuvant in contact therewith and to allow release of the drug and adjuvant. No other particular limitations are placed on said substance. However, a synthetic resin and/or a rubber having a Tg of −70° C. to −10° C. is a preferred macromolecular substance.

When the macromolecular substance has a Tg of not lower than −70° C., the base composition has an increased shape-holding property, leaves no residue on the skin and causes no skin irritation at the time of peeling off. Accordingly such material is preferred. That the Tg of the macromolecular substance is not higher than −10° C. is desirable because of improvement in adhesion to the skin.

The most preferable Tg range is −55° C. to −18° C. A macro-molecular substance having a Tg within the range of −70° C. to −10° C. may be selected from the group consisting of the following synthetic resins and rubbers.

The synthetic resins include polyvinyl alkyl ether, poly(meth)acrylate, polyurethane, polyester, polyamide, ethylene-vinyl acetate copolymer, and so on.

The rubbers include styrene-isoprene-styrene block copolymer rubber, styrene-butadiene rubber, polybutene rubber, polyisopren rubber, butyl rubber, silicone rubber, natural rubber, and so forth.

In case a desired Tg value cannot be obtained with a single member of each of the above subgroups, the member may be used in combination with a member of the other subgroup or a well known additive may be added so as to adjust the Tg to a required value.

Experiments by the present inventors have revealed that acrylic copolymers are the most satisfactory macromolecular substances in that they can meet the above-mentioned requirements with regard to close adhesion, compatibility, solubility and releasability in a most reliable manner by a relatively simple manufacturing procedure.

Preferred acrylic copolymers have the following composition

Said copolymers are acrylic copolymers containing at least 50 weight percent of an alkyl (meth)acrylate in which the average number of carbon atoms contained in the alkyl group is not less than 4. The "average number of carbon atoms" as used herein means the weight average number of carbon atoms contained in the ester moieties when two or more alkyl esters different in the number of carbon atoms in the alkyl moiety are used. The preferred number of carbon atoms in the alkyl moiety is 2-12.

Said copolymers are favorable with respect to close adhesion to the skin and solubility of the drug and adjuvant. They scarcely irritate the skin and hold the drug and adjuvant stably.

The above copolymers also include copolymers of an alkyl (meth)acrylate with a functional monomer copolymerizable therewith. Such monomer is used in ah amount of 0-20 weight percent, preferably 0.5-15 weight percent. The functional monomer includes acrylic acid, methacrylic acid, maleic acid, maleic anhydride, itaconic acid, acrylamide, methacrylamide, acrylonitrile, glycidyl acrylate, hydroxyalkyl acrylate, alkoxy acrylate etc.

Since the cohesiveness of the copolymers can be varied by varying the level of addition of said monomer, the rates of release or release amounts of the drug and adjuvant from the base can be controlled. Furthermore, the hydrophilic property of the copolymers may be increased by adequate selection of said monomer. For instance, the hydrophilic property can be increased by varying the weight ratio of octyl acrylate to acrylic acid in copolymerization thereof from 95:5 to 85:15.

The hydrophilic property can further be increased by using ethyl acrylate in place of the above octyl acrylate.

The above-mentioned copolymers further include copolymers of an alkyl (meth)acrylate with a vinyl ester monomer copolymerizable therewith in an amount of 0-40 weight percent, preferably 10-30 weight percent. The drug and adjuvant are highly soluble in the copolymers containing such monomer. Examples of said vinyl ester monomer are vinyl acetate and vinyl propionate.

In view of the foregoing, it will readily be understood that those acrylic copolymers mainly composed of at least 50 weight percent of an alkyl (meth)acrylate, 0-20 weight percent of the above functional monomer copolymerizable therewith and 0-40 weight percent of the above vinyl ester monomer copolymerizable with the above ester are suited as the macromolecular substances for carrying the adjuvant and drug.

Furthermore, for improvement in shape-holding property or adhesiveness or for controlled release of the drug, the above-mentioned macromolecular substance layer and polymer layer each may be crosslinked, for example, by using a chemical crosslinking agent or by irradiation with ultraviolet light or electron rays.

By the "adjuvant" is meant a substance capable of directly or indirectly increasing percutaneous absorption of the drug. The adjuvant which directly causes increased percutaneous absorption is, for example, an absorption promoter having the function of providing the horny layer (skin) with water-holding property, accelerating the swelling or hardening of the horny layer, increasing the wettability of the horny layer and/or opening pores of the skin. In many cases, one substance can have a plurality of such functions.

The adjuvant which indirectly promotes percutaneous absorption is, for example, a substance capable of causing increased diffusion of the drug in each layer or increasing the solubility of the drug in each layer.

Examples of the adjuvant for indirect increase in percutaneous absorption are liquid paraffin, vaseline, lanolin, olive oil, glycerin, benzyl alcohol, butyl benzoate, isopropyl myristate, octanol, 1,3-butanediol, (poly)-propylene glycol, (poly)ethylene glycol, other alcohols and surface active agents, and oligomers such as low-molecular-weight (number average molecular weight=not greater than 30,000) polyacrylate, polymethacrylate and polyvinyl ethers.

Examples of the adjuvant for direct increase in percutaneous absorption are dimethyl sulfoxide, dodecyl sulfoxide, methyl octyl sulfoxide, dimethyl decyl phosphoxide, mono- or diethylacetamide, N-hydroxyethyllactamide, dimethylacetamide, N,N-dimethyldodecamide, dimethylformamide, diethyltoluamide, tetrahydrofurfuryl alcohol, tetrahydrofuran, sorbitol, dodecylpyrrolidone, methylpyrrolidone, urea, diethyl adipate, squalene, acetylated lanolin, cetyl lactate, dioctyl sebacate, ethoxylated stearyl alcohol, lanolinic acid, lanolinyl alcohol, higher fatty alcohol, salicylic acid, liquid paraffin, vaseline, amino acids, protease, methyl nicotinate, l-menthol, camphor, salocolum, sodium lauryl sulfate, sodium laurate, stearin, glycerol stearate, higher fatty acid triglyceride, polyoxyalkylene glycol, fatty acid mono(or di)ethanolamide, ethylene glycol monoethyl ether, polyoxypropylene alkyl ether, higher alkyl sulfone, etc.

The drug may be any one percutaneously absorbable to a therapeutically effective concentration by itself or with the assistance of a percutaneous absorption promoter (adjuvant). No other particular limitations are placed thereon. Thus, it includes, among others, the following:

a) Corticoids: hydrocortisone, prednisolone, paramethasone, beclomethasone propionate, flumethasone, betamethasone, dexamethasone, triamcinolone, triamcinolone acetonide, fluocinolone, fluocinolone acetonide, fluocinolone acetonide acetate, clobetasol propionate, etc.;
b) Analgesics and antiinflammatory agents: acetaminophen, mefenamic acid, flufenamic acid, indomethacin, diclofenac, alclofenac, oxyphenbutazone, phenylbutazone, ibuprofen, flurbiprofen, salicylic acid, l-menthol, camphor, combinations thereof, etc.;
c) Hypnotics and sedatives: barbiturates such as phenobarbital amobarbital and cyclobarbital, etc.;
d) Tranquilizers: fluphenazine, thioridazine, benzodiazepines (e.g. diazepam, lorazepam, flunitrazepam), chlorpromazine, etc.;
e) Antihypertensive agents: clonidine, kallikrein, etc.;
f) Hypotensive and diuretic agents: hydrothiazide, bendroflumethiazide, etc.;
g) Antibiotics: beta-lactam antibiotics (penicillins and cephalosporins), oxytetracycline, fradiomycin sulfate, erythromycin, chloramphenicol, etc.;
h) Anesthetics: lidocaine, benzocaine, ethyl aminobenzoate, etc.;
i) Antibacterial agents: nitrofurazone, nystatin, acetosulfamine, clotrimazole, etc.;
j) Antifungal agents: pentamycin, amphotericin B, pyrrolnitrin, clotrimazole, etc.;
k) Vitamins: vitamin A, ergocalciferol, cholecalciferol, octotiamine, riboflavine butyrate, etc.;
l) Epileptics: nitrazepam, meprobamate, etc.;
m) Coronary vasodilators: nitroglycerin, nifedipine, dipyridamole, isosorbide dinitrate, erythritol tetranitrate, pentaerythritol tetranitrate, etc.; and
n) Antihistminics diphenhydramine hydrochloride, chlorpheniramine, diphenylimidazole, etc.

As necessary, these drugs may be used in combination of two or more of them.

Furthermore, a filler may be formulated as an optional component for retaining the shape-holding property of the macromolecular substance layer. Small amounts of common additives such as adhesiveness-imparting resin and softening agent may also be added to said layer.

The filler includes finely divided silica, titanium white, calcium carbonate, etc. The filler may be added in an amount of not more than 30 weight percent based on the composition. The adhesiveness-imparting resin includes rosin, hydrogenated rosin, rosin ester, polyterpene resin, aliphatic or aromatic petroleum resin, coumarone-indene resin, xylene resin, terpene-phenol resin, etc.

The softening agent includes polybutene, abietyl alcohol, liquid paraffin, liquid resin, etc.

The amount of the drug to be contained in the preparation of the invention depends on the kind of drug, solubility thereof in the macromolecular substance and in the polymer, thickness of each layer and other factors. Generally, the amount is about 0.1–20 weight percent, preferably 0.5–15 weight percent, based on the total weight of both the layers. The adjuvant is used generally in an amount of 1–30 weight percent, preferably 3–20 weight percent, on the same basis.

The macromolecular substance layer generally has a thickness of 5–500 microns, preferably 20–200 microns, and the polymer layer generally has a thickness of 10–1,000 microns, preferably 30–500 microns.

The macromolecular substance layer is formed on the whole or part of the polymer layer.

The preparation of the invention is produced, for example, by directly applying a macromolecular substance layer-forming composition to the polymer layer or by preliminarily forming a macromolecular substance layer on a release liner followed by transfer of said layer onto the polymer layer for lamination.

Since the preparation of the invention contains the drug and adjuvant in the respective different layers, the preparation can contain greater amounts of drug and adjuvant as compared with the case where the drug and adjuvant are contained in a single layer. Furthermore, even when the macromolecular substance layer or polymer layer contains the drug in an amount exceeding the solubility limit, the excess drug can migrate into the polymer layer or macromolecular substance layer, respectively, before crystallization thereof takes place. Such migration of course can occur also when the amount of the drug is below the solubility limit.

Similarly, the adjuvant also migrates from the layer originally containing the same to the other layer not only in the case of addition at a level exceeding the solubility limit but also in the case of addition at a level below the solubility limit.

As a result, neither the drug nor the adjuvant can crystallize out in the preparation of the invention.

The composite preparation of the invention is applied to the skin at an adequate site, where the drug in the macro-molecular substance layer is gradually absorbed through the skin and at the same time the adjuvant is partly absorbed and partly migrates. The thus-caused change in the adjuvant ratio and drug ratio in the macromolecular substance layer in turn induces supply of the drug and adjuvant from the polymer layer to the macromolecular substance layer so as to compensate for the decrease in the amounts the drug and adjuvant. The effects thus producible are equivalent to substantial increases in the amounts of the drug and adjuvant per unit area of the composite preparation.

Accordingly, a fast-acting composite preparation can be obtained by satisfying the relation that the solubility of the drug in the macromolecular substance layer is much greater than the solubility of the drug in the polymer layer and the relation that the macromolecular substance layer thickness is smaller than the polymer layer thickness; a slow-acting composite preparation can be produced when the relation that the solubility of the drug in the macromolecular substance layer is much smaller than the solubility of the drug in the polymer layer and the relation that the macro-molecular substance layer thickness is smaller than the polymer layer thickness are satisfied; and furthermore a fast- and long-acting composite preparation can be obtained if the drug is contained in the macromolecular substance layer and polymer film at the respective levels of saturation (with the solubility of the drug in the macromolecular substance layer being greater than that in the polymer layer)and the macromolecular substance layer thickness is smaller than the polymer film thickness. In addition, as can readily be understood, the drug release can be finely controlled by combinedly utilizing the difference in solubility of the drug and adjuvant between the macromolecular substance layer and polymer layer, the equilibrium resulting therefrom and the miscibility of the adjuvant with the drug.

It is to be understood that the preparation of the invention also covers the mode in which both the macromolecular substance layer and polymer layer contain the drug and adjuvant as a result of migration of the drug and/or adjuvant and further the mode in which one of the layers contains the drug and adjuvant and the other contains one of the drug and adjuvant.

The following examples illustrate the invention in more detail, wherein "part(s)" means "parts(s) by weight".

EXAMPLE 1

A three-necked flask is charged with 96 g of isooctyl acrylate, 4 g of acrylic acid and 25 g of ethyl acetate containing 0.2 g of azobisisobutyronitrile. After purging with an inert gas, the mixture is heated in the inert gas atmosphere to 60° C. for initiation of reaction, and the reaction is carried out at 62°-65° C. for 5 hours with dropwise addition of ethyl acetate and further at 75°-77° C. for 2 hours for aging. A copolymer solution having a solid content of 30% by weight and a viscosity of 195 poises as measured at 30° C. is obtained.

Flunitrazepam is added to the above solution in an amount of 5.0 parts per 100 parts of the solid in said solution. The resulting mixture is applied to a release liner to an extent such that the coated layer after drying has a thickness of 60 microns. Drying of the coated layer gives a base film (Tg −55° C.).

Separately, a laminated film is prepared by laminating a 50-micron-thick ethyl acrylate-vinyl acetate copolymer film (ethyl acrylate:vinyl acetate weight ratio =2:1; Tg −13° C.) containing 4 weight percent of diethyl sebacate as the polymer film layer, into which the drug and adjuvant can migrate, onto one side of a 12.7-micron-thick corona-treated polyester film.

The above base film is placed on and pressed against the copolymer film layer side of the laminated film. A composite preparation is thus obtained.

EXAMPLE 2

To the copolymer solution as used in Example 1, there is added 7 parts of propatyl nitrate per 100 parts of the solid in said solution and the resulting mixture is applied to a release liner to a thickness (after drying) of 40 microns. Drying gives a base film (Tg −55° C.).

Separately, a 100-micron-thick laminated film is produced by coextrusion of a mixture (Tg −25° C.) of an ethylene-vinyl acetate copolymer (vinyl acetate content 40 weight %) and 10 parts by weight of olive oil and polyethylene (EVA film layer thickness 40 microns).

The above base film is placed on and pressed against the copolymer film layer side of the laminated film. A composite preparation is thus obtained.

EXAMPLE 3

A composition composed of 45 parts of polyisoprene rubber, 15 parts of liquid paraffin, 10 parts of lanoline and 30 parts of an aliphatic petroleum resin is heated under an inert gas at 110°-125° C. for 5 hours for dissolution and then cooled to 80° C. Then, thereto is added 5 parts of indomethacin as a dispersion in 7 parts of propylene glycol. The resulting mixture is applied to a release liner to a thickness of 100 microns. There is obtained a base film (Tg −18° C.).

Separately, a laminated film is prepared by laminating with heating under pressure a 40-micron-thick film made of a vinyl acetate-butyl acrylate-methoxyethyl acrylate (40:30:30 weight ratio) copolymer (Tg −33° C.) containing 4 weight percent of ethylene glycol monosalicylate to a 50-micron-thick polyvinylidene chloride film.

The above drug-containing base film is placed on and pressed against the copolymer film layer side of the laminated film. There is thus obtained a composite preparation.

Tables 1-3 show the test results for the composite preparations of Examples 1-3. Table 1 shows, for each preparation, the time for the drug to crystallize out. Table 2 shows the adhesiveness to the skin, the preparation-to-Bakelite plate adhesive strength and durability of the adhesive bond. Table 3 illustrates the blood level of the drug at timed interval after application of each sample. Comparative examples 1-3 in Tables 1 and 2 correspond to Examples 1-3, respectively, and therefore the samples were prepared by laminating under pressure the respective base films to a polyester film, a polyethylene film and polyvinylidene chloride film, respectively, without using any polymer layer.

TABLE 1

| | Storage period | | | | | |
|---|---|---|---|---|---|---|
| | 1 day | 3 days | 5 days | 10 days | 30 days | 90 days |
| Example 1 | No | No | No | No | No | No |
| Comparative Example 1 | No | No | Partly | Partly | Partly | About half |
| Example 2 | No | No | No | No | No | No |
| Comparative Example 2 | No | Partly | About half | Mostly | Mostly | Mostly |
| Example 3 | No | No | No | No | No | No |
| Comparative Example 3 | Partly | Partly | About half | About half | About half | About half |

Notes: Storage conditions: 25° C. × 65% R.H. No - No crystallization; Partly, etc. - Partly crystallized, etc.

TABLE 2

| | Adhesion to Skin Storage Days | | | Adhesion to Bakelite Plate (g/12 mm) Storage Days | | | Retention to Bakelite Plate (min) Storage Days | | |
|---|---|---|---|---|---|---|---|---|---|
| | 1 Day | 10 Days | 90 Days | 1 Day | 10 Days | 90 Days | 1 Day | 10 Days | 90 Days |
| Example 1 | good | good | good | 620 | 620 | 600 | 17 | 15 | 18 |
| Comparative Example 1 | good | fair | bad | 650 | 490 | 410 | 17 | break | break |
| Example 2 | good | good | good | 620 | 610 | 600 | 13 | 12 | 15 |
| Comparative | good | fair | bad | 600 | 300 | 60 | 20 | break | break |

TABLE 2-continued

| | Adhesion to Skin Storage Days | | | Adhesion to Bakelite Plate (g/12 mm) Storage Days | | | Retention to Bakelite Plate (min) Storage Days | | |
|---|---|---|---|---|---|---|---|---|---|
| | 1 Day | 10 Days | 90 Days | 1 Day | 10 Days | 90 Days | 1 Day | 10 Days | 90 Days |
| Example 2 | | | | | | | | | |
| Example 3 | good | good | good | 400 | 410 | 390 | 50 | 40 | 43 |
| Comparative Example 3 | good | fair | bad | 410 | 390 | 260 | 40 | 170 | break |

Methods for measuring adhesion and retention shown in Table 2 are as follows.

Adhesion to Bakelite Plate

A 12 mm wide sample was applied to a bakelite plate and press bonded thereonto by rolling back and forth, one time, a 2.0 kg rubber roller. After storing for 30 minutes, the sample was peeled at one end from the plate to determine the adhesion (peeling angle: 180°; peeling speed: 300 mm/min; 20° C., 65%RH).

Retention

One end of a sample (width: 10 mm; length: 100 mm) was applied to an end of a Bakelite plate by 20 mm and, after storing for 20 minutes, a 300 g load was applied to the other end of the sample to measure the time by which it was fallen down from the Bakelite plate (at 40° C.).

Additionally, "break" in Table 2 indicates interlayer break between the base material layer and the film layer or interfacial break from the Bakelite plate.

TABLE 3

| | Blood level (in ng/ml) after application for (hours) | | | | | | |
|---|---|---|---|---|---|---|---|
| | 0.5 | 1 | 2 | 5 | 10 | 24 | 48 |
| Example 1 | 7 | 14 | 16 | 14 | 19 | 18 | 13 |
| Comparative Example 1 | ~1 | 4 | 7 | 9 | 7 | 6 | 4 |
| Example 2 | 3 | 6 | 7 | 8 | 9 | 8 | 3 |
| Comparative Example 2 | 2 | 3 | 3 | 4 | 3 | 3 | 2 |
| Example 3 | 3 | 9 | 9 | 10 | 16 | 19 | 15 |
| Comparative Example 3 | 0 | 2 | 2 | 5 | 4 | 4 | 1 |

Blood level determination

Each composite medicinal preparation (6 cm×6 cm) was adhered to the clipped back of each rabbit (weighing 2 kg) and blood sampling (3 ml) was conducted at specified intervals. For flunitrazepam:

To 1 ml of blood were added 2 ml of saturated ammonium chloride and 6 ml of 8:2 toluene-heptane. After shaking for 15 minutes, the mixture was centrifuged, the organic layer was extracted with 6N HCl, and the extract fraction separated by centrifugation was neutralized with 6N NaOH under ice cooling. Thereto was added 5 ml of the above solvent mixture, the organic layer was evaporated, and the residue was dissolved in 250 μl of ethanol and analyzed by gas chromatography using prazepam as the internal standard. For propatyl nitrate:

Blood was sampled (3 ml), the plasma was separated and extracted with 2 ml of n-hexane, and the extract separated by centrifugation was concentrated to 0.5 ml under an inert gas. The concentrate was further extracted with 1 ml of acetonitrile, the acetonitrile layer was concentrated to dryness under an inert gas, and the residue was dissolved in 100 μl of benzene and assayed by gas chromatography. For indomethacin:

To 1 ml of plasma was added 2 ml of 0.5M citrate buffer (pH 5.0) and the mixture was extracted with 10 ml of 1,2-dichloroethane. Following addition of 2,4,6-triphenylnitrobenzene as the internal standard to the organic layer, the solvent was distilled off and then diazomethane was added. The reaction mixture was analyzed for indomethacin methyl ester by gas chromatography.

EXAMPLE 4

A three-necked flask is charged with 93 g of isooctyl acrylate, 7 g of acrylic acid and 25 g of ethyl acetate containing 0.2 g of azobisisobutyronitrile. After purging with an inert gas, the mixture is heated in the inert gas atmosphere to 60° C. for initiation of reaction, and the reaction is carried out at 62°-65° C. for 7 hours with dropwise addition of ethyl acetate and the reaction mixture is further maintained at 75°-77° C. for 2 hours for aging. There is obtained a copolymer solution having a viscosity of 460 poises (30° C.) and a solid content of 30% by weight.

To this solution is added diethyl adipate in an amount of 7 parts per 100 parts of the solid in said solution. The resulting mixture is applied to a release liner to a thickness (after drying) of 30 microns Upon drying, there is obtained a base film (Tg −50° C.)

Separately, a laminated film is prepared by laminating a 50-micron-thick ethyl acrylate-vinyl acetate copolymer film (ethyl acrylate vinyl acetate weight ratio=3:1; Tg −17° C.) containing 5 weight percent of flunitrazepam as the polymer film layer, into which the adjuvant and drug can migrate, to one side of a 12.7-micron-thick polyester film.

The above base film is adhered to the copolymer film layer side of the laminated film under pressure to give a composite preparation.

EXAMPLE 5

To the copolymer solution as used in Example 4, there are added 2 parts of ethylene glycol monosalicylate and 4 parts of propylene glycol per 100 parts of the solid in said solution and the resulting mixture is applied to a release liner to a thickness (after drying) of 40 microns. A base film is thus obtained.

Separately, a 100-micron-thick laminated film is prepared by coextruding an ethylene-acrylic acid copolymer (acrylic acid content 12% by weight; Tg −10° C.) containing 5 weight percent of indomethacin and polyethylene (copolymer film thickness 50 microns).

The above base film is adhered under pressure to the copolymer film layer side of the laminated film to give a composite preparation.

EXAMPLE 6

A composition composed of 45 parts of polyisoprene rubber, 15 parts of liquid paraffin, 10 parts of lanoline and 30 parts of an aliphatic petroleum resin is heated under an inert gas at 110°-125° C. for 5 hours for dissolution and then cooled to 80° C. Thereafter, 8 parts of dimethyl sulfoxide is added and the resulting mixture is applied to a release liner to a thickness of 50 microns. There is obtained a base film (Tg −48° C.).

Separately, a laminated film is prepared by laminating with heating under pressure a 40-micron-thick film made of polyvinyl acetate (Tg 33° C.) containing 12 weight percent of propatyl nitrate to a 50-micron-thick polyvinylidene chloride film.

The above base film is adhered under pressure to the polyvinyl acetate film layer side of the laminated film to give a composite preparation.

Tables 4-5 show the test results for the composite preparations of Examples 4-6. For each preparation, Table 4 shows the time for the drug to crystallize out and Table 5 shows the blood level of the drug in the rabbit. Comparative Examples 4-6 in Tables 4-5 correspond to Examples 4-6 and refer to the cases where the respective polymer layers alone were used. In the comparative examples, the samples were fixed with an adhesive tape where they were difficult to adhere to the skin.

The blood level determination was performed in the same manner as mentioned for Examples 1-3.

TABLE 4

| | Storage period | | | | |
|---|---|---|---|---|---|
| | 1 day | 2 days | 4 days | 10 days | 30 days |
| Example 4 | No | No | No | No | No |
| Comparative Example 4 | Partly | About half | Mostly | Crystallized | Crystallized |
| Example 5 | No | No | No | No | No |
| Comparative Example 5 | No | Partly | About half | Mostly | Mostly |
| Example 6 | No | No | No | No | No |
| Comparative Example 6 | No | Partly | About half | About half | About half |

Notes: Storage conditions, 25° C. · 65% R.H. No - No crystallization. Partly, etc. - Partly crystallized, etc.

TABLE 5

| | Blood level (in ng/ml) after application for (hours) | | | | | | |
|---|---|---|---|---|---|---|---|
| | 0.5 | 1 | 2 | 5 | 10 | 24 | 48 |
| Example 4 | 3 | 8 | 18 | 22 | 22 | 21 | 7 |
| Comparative Example 4 | 0 | 2 | 6 | 7 | 6 | 3 | 4 |
| Example 5 | 1 | 3 | 8 | 9 | 7 | 8 | 7 |
| Comparative Example 5 | 0 | 0 | 3 | 3 | 4 | 4 | 4 |
| Example 6 | 5 | 10 | 15 | 18 | 15 | 16 | 12 |
| Comparative Example 6 | 2 | 4 | 4 | 3 | 2 | 1 | 1 |

We claim:

1. A process for the preparation of a pressure-sensitively adhering composite medicinal preparation which (1) comprises at least two layers, said layers being (a) a layer of a macromolecular substance, whose glass transition point is within the range from −70° C. to −10° C., having pressure-sensitive adhesiveness at ordinary temperatures and (b) a polymer layer, whose glass transition point is within the range from −50° C. to 75° C., said polymer layer being adjacent to said macromolecular substance layer, (2) one of the said layers (a) and (b) contains a percutaneously absorbable drug and other of said layers contains an adjuvant capable of increasing percutaneous drug absorption, and (3) the drug and adjuvant respectively can immigrate into the adjacent macromolecular substance layer and polymer layer, the process comprising lamenating one of layer (a) and (b) which contains a percutaneously absorbable drug to the other layer which contains an adjuvant capable of increasing percutaneous drug absorption.

2. The process of claim 1, wherein the macromolecular substance layer containing the drug is laminated to the polymer layer containing the adjuvant.

3. The process of claim 1, wherein the macromolecular substance layer containing the adjuvant is laminated to the polymer layer containing the drug.

4. The process of claim 1, wherein the polymer layer contains at least 10 weight percent of a polymer having a glass transition point of not lower than −50° C.

5. The process of claim 4, wherein the polymer having a glass transition point of not lower than −50° C. comprises at least one member selected from the group consisting of polyvinyl acetate, copolymers of vinyl acetate and a monomer copolymerizable therewith, and polymers containing an alkoxy (meth)acrylate.

6. The process of claim 1, wherein the macromolecular substance is an acrylic copolymer.

7. The process of claim 6, wherein the acrylic copolymer is an acrylic copolymer containing at least 50 weight percent of an alkyl (meth)acrylate, the average number of carbon atoms contained in the alkyl group of said alkyl (meth)acrylate being not smaller than 4.

8. The process of claim 6, wherein the (meth)acrylic copolymer is composed of at least 50 weight percent of an alkyl (meth)acrylate, not greater than 20 weight percent of a function copolymerizable with said (meth)acrylate and not greater than 40 weight percent of a vinyl ester monomer copolymerizable with said ester.

9. The process of claim 1, wherein the content of the drug is 0.1-20% by weight based on the total weight of the macromolecular substance layer and polymer layer and the adjuvant content is 1-30% by weight on the same basis.

10. The process of claim 1, wherein the macromolecular substance layer has a thickness of 5-500 microns and the polymer layer has a thickness of 10-1,000 microns.

11. The process of claim 1, wherein a film or sheet substantially impermeable to the drug and adjuvant is provided on the side of the polymer layer opposite the macromolecular substance layer.

* * * * *